United States Patent [19]

Crosby et al.

[11] 4,055,678
[45] Oct. 25, 1977

[54] SWEETENER DERIVATIVES

[75] Inventors: Guy A. Crosby; Grant E. DuBois, both of Palo Alto, Calif.

[73] Assignee: Dynapol, Palo Alto, Calif.

[21] Appl. No.: 648,423

[22] Filed: Jan. 12, 1976

Related U.S. Application Data

[62] Division of Ser. No. 477,730, June 10, 1974, Pat. No. 3,976,687.

[51] Int. Cl.$^2$ ............................................. A23L 1/236
[52] U.S. Cl. ................................. 426/548; 260/511
[58] Field of Search ............. 426/548; 260/511, 520, 260/473 G, 592

[56] References Cited

U.S. PATENT DOCUMENTS

| 3,739,064 | 6/1973 | Rizzi | 426/548 X |
| 3,876,816 | 4/1975 | Zaffaroni | 426/548 |
| 3,974,299 | 8/1976 | Crosby et al. | 426/548 |
| 3,976,790 | 8/1976 | Crosby et al. | 426/590 X |

FOREIGN PATENT DOCUMENTS

CI 1196  1/1973  Hungary ................................ 426/548

Primary Examiner—Raymond N. Jones
Assistant Examiner—Esther M. Kepplinger
Attorney, Agent, or Firm—William H. Benz

[57] ABSTRACT

Dihydrochalcones of the formula

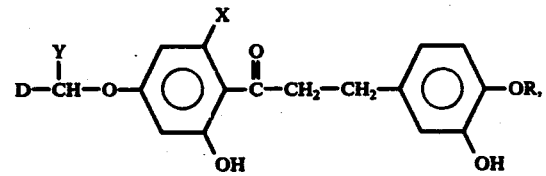

derivatizing group, Y is a polar group, X is hydrogen or hydroxyl and R is a lower alkyl, their preparation and their use as non-sugar sweeteners are disclosed.

9 Claims, No Drawings

SWEETENER DERIVATIVES

This is a division of application Ser. No. 477,730 filed June 10, 1974, now U.S. Pat. No. 3,976,687, issued Aug. 24, 1976.

BACKGROUND OF THE INVENTION

1. Field of the Invention.

This invention relates to compositions for imparting sweetness to edible compositions such as foodstuffs.

2. Reference to Related Application

This application is related to U.S. Pat. No. 3,974,299 issued Aug. 10, 1976 to the present inventors and concerning nonderivatized forms of some of the present dihydrochalcones.

THE PRIOR ART

Dihydrochalcones are compounds having a

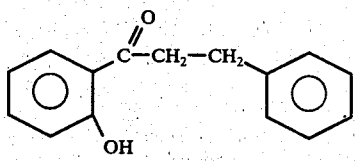

basic structure.

A range of dihydrochalcone materials, both natural and synthetic, has been disclosed in the prior art. These materials vary from one another by the nature and placement of substituents on the aromatic rings.

A limited number of the dihydrochalcones, such as those disclosed in Horowitz and Gentili's U.S. Pat. Nos. 3,087,871 (issued Apr. 30, 1963) and 3,583,894 (issued June 8, 1971), and Farkus et al's Hungarian Patent Application, CI-1196, have taken on special interest because they are sweet. They appear to be nontoxic and potentially attractive as nonsugar sweeteners — offering the advantages of being essentialy noncaloric, not having an insulin requirement, and sometimes being relatively "sugar-like" in taste.

As pointed out in the cited Horowitz and Gentili patents and their chapter in the Book *Sweeteners and Sweetness;* Birch, Green, and Coulson, Eds, Applied Science Publishers, Ltd., London, pp. 69–77 (1971), the dihydrochalcones' sweetness depends upon the nature of the aromatic ring substituents and their exact location on the rings. A change which is relatively minor from a chemical structure point of view will very often have a major effect on the taste properties of the dihydrochalcone product. No broadly applicable rules have been developed to show or predict whether new dihydrochalcones will be sweet or not. This extreme sensitivity of taste and structure makes the formation of derivatives of dihydrochalcones very difficult when a retention of sweetness is desired. This means that as a rule under prior art teachings, it is really not possible to vary by derivatization the molecular size or properties, such as its polarity or solubility, of a dihydrochalcone without jeopardizing the sweetness properties of the material. As it is often of interest to make minor variations in a sweet molecule's nonflavor properties to enhance its usefulness as a sweetener, this inability is a real problem.

STATEMENT OF THE INVENTION

While studying a group of sweet dihydrochalcones, themselves believed to be new compounds, a point at which derivatization may be effected without destroying the compound's sweetness has been discovered. More particularly, it has been found that sweet dihydrochalcones represented by General Formula (I):

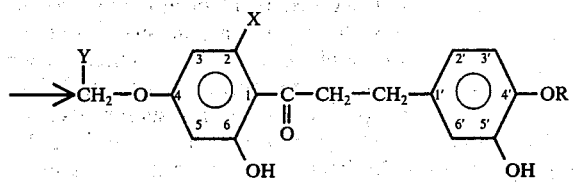

wherein Y is a polar group, X is hydrogen or hydroxyl, and R is a lower saturated alkyl, can be derivatized at the methylene link intermediate polar group Y and the oxy bridge of their 4 substituent. This position is indicated in General Formula (I) by an arrow. Derivatization takes place by replacing one of said methylene link's hydrogens with a derivatizing group, D. When sweet dihydrochalcones are derivatized in accord with this invention, they retain their sweetness. The derivatized dihydrochalcones are represented by General Formula (II),

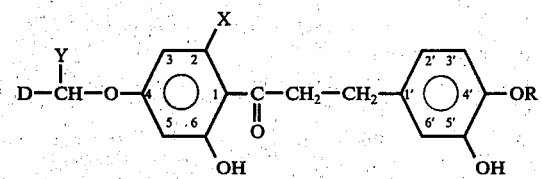

wherein Y, X and R are as already defined, and D is a derivatizing group.

DETAILED DESCRIPTION OF THE INVENTION

The Dihydrochalcones

The dihydrochalcones which are derivatized in accordance with this invention have the set chemical structure shown in General Formula (I). In their derivatized form, they have the structure shown in General Formula (II). As shown in these formulae, they contain a lower saturated alkoxy group at their 4' position. This alkoxy group is selected from among methoxy, ethoxy, propoxy, and butoxy groups (including the various propoxy and butoxy isomers). Preferably the 4' position carries a methoxy or isopropoxy, with methoxy being the most preferred 4' substituent. At the 4 position they contain a methoxy group, to which is attached a polar group Y. Polar group Y may include, for example, a carboxylic acid group (—COOH); a carboxylic acid salt (—COOM, wherein M is a pharmacologically acceptable cation such as the pharmacologically acceptable alkali metal, alkaline earth, ammonium and transition metal cations, especially sodium and potassium cations); a hydroxyl group (—OH); a primary amide group (—CONH$_2$); a sulfonic acid group (—SO$_3$H) or a sulfonic acid salt (SO$_3$M, wherein M is as defined above). Among the polar groups the carboxylic and sulfonic acids and their corresponding —COOM and —SO$_3$M salts are preferred, with the carboxylic acid and its sodium salt comprising most preferred polar groups.

DERIVATIZATION AND DERIVATIZING GROUPS

A derivatizing group, D, is present as a substituent on the 4 position methoxy group. D groups must be organic, containing at least one carbon atom. Suitable derivatizing groups include any group which, when covalently attached to the dihydrochalcone, brings about a useful change in its properties, such as its solubility in aqueous media, its ability to crystallize, its diffusivity or permeability through membranes, or its sweet flavor characteristics. When it is desired to increase the dihydrochalcones' solubility in aqueous media, derivatizing group D is selected from hydrophilic organic groups, such as linear polyethers, for example, the polyethoxyethers (CH$_3$[—O—CH$_2$—CH$_2$]$_n$—O) (wherein $n$ is from about 1 to about 30) marketed by Union Carbide under the name "Carbowax" and polyethylene glycol; polyhydroxy materials, for example, polyhydroxy-substituted polymethylene chains as found in polyvinyl alcohol; and polyhydroxy-substituted ethers, for example, polyglycidol. A preferred class of derivatizing groups D are saturated hydrocarbons and oxyhydrocarbons having from 1 to 6 carbons and 0 to 3 oxygens. These include lower alkyls such as methyl, ethyl, butyl, cyclohexane and the like; alkoxy groups such as methoxy, ethoxy and isobutoxy; and lower polyethoxy ethers.

In a special application, derivatizing group D is a group which increases the molecular bulk or size of the dihydrochalcone molecule to an extent that the molecule is too large to pass through the walls of the gastrointestinal tract and thus is not absorbable into the body when ingested. While to date no severe toxicological problems have been associated with the dihydrochalcones, rendering them nonabsorbable by this derivatization would eliminate any question of danger. As a general rule, a group D should have a molecular weight of at least about 700 to render a dihydrochalcone molecule too large to be absorbable. Preferably in this application, D has a molecular weight of from 100 to 10,000, although larger materials can be used, if desired.

In anoher embodiment of this invention, group D serves as a bridge or link between two or more dihydrochalcones of the type described herein. Such a product is represented by Formula (III),

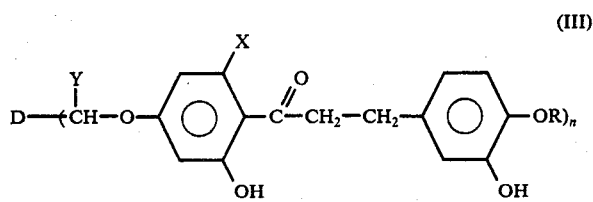

(III)

wherein Y, n, D, and R are as defined in Formula (II) and n is an integer greater than 1, preferably from 2 to 20, and more preferably from 2 to 15. With such a material, the plurality of dihydrochalcone groups itself contributes to a large molecular size and can render the molecule large enough to not be absorbed through the walls of the gastrointestinal tract, if such property is sought.

The derivatizing group, D, is covalently bonded to the dihydrochalcone. In its attachment to the dihydrochalcones, the D group displaces one of the hydrogens on the dihydrochalcone's 4-position methoxy group.

Preparation

The derivatized dihydrochalcones of this invention may be produced by alkylating a flavanone such as hesperetin with a polar group and derivatizing group-containing agent and thereafter opening and reducing the alkylation product to the desired dihydrochalcone. This preparation is illustrated as follows:

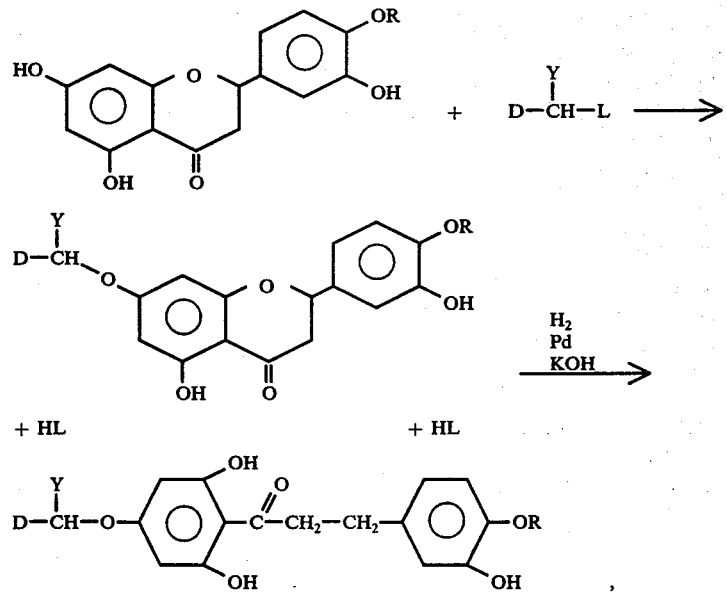

wherein D, Y and R are as hereinabove set forth and L is a leaving group such as chloride, tosylate, iodide, bromide, methylate, or the like.

The alkylation reaction is best carried out in a reaction solvent inert to the reactants and conditions employed, such as dimethylformamide, tetrahydrofuran, glyme, acetone, or hexamethylphosphoramide. This reaction is often carried out in the presence of an added leaving group scavenger which reacts with liberated leaving groups and prevents their buildup in the reaction mixture. As an example, when Br⁻ is the leaving group, a weak inorganic base such as $K_2CO_3$, $Na_2CO_3$, or $K_3PO_4$ may be added to form KBr or NaBr, which precipitates from the reaction mixture, avoiding buildup. This reaction may be carried out at mild conditions such as at temperatures of from about room temperature (20° C) up to about 100° C.

The opening and hydrogenation reaction is carried out by a strong base and hydrogenation conditions. Any strong base, for example, sodium hydroxide, lithium hydroxide, or tetramethyl ammonium hydroxide may be used. The hydrogenation may be carried out catalytically as shown, in the presence of a suitable transition metal or precious metal catalyst (such as nickel, cobalt, platinum or palladium catalysts) and molecular hydrogen at pressures from atmospheric up to as much as about 100 psig and temperatures of from about room temperature (20° C) up to about 125° C; or it may be effected by reaction with a hydrogen-carrying agent such as diimide.

Use of the Dihydrochalcones

These derivatized dihydrochalcones find application as sweeteners. In this use they are admixed with edible substances such as food, beverages, medicines, and the like, in amounts effective for imparting a desired degree of sweetness. The amount of dihydrochalcone employed can vary widely, just as the amount of natural sugar sweetener varies from person to person and food application to food application. As a general rule, the weight of derivatized dihydrochalcone added will be about 1/100 – 1/500 the weight of sucrose required to yield the same sweetness. Thus, additions of from say 0.0001% up to about 0.05% by weight (basis edible substance) may usefully be employed.

The derivatized dihydrochalcones are added to the edible composition by mixing methods known in the art. They may be added as solids or as solutions. They may be used alone or as the primary sweetener in a composition, or they may be one of several sweeteners in the final composition; sucrose, or another natural sweetener, or another synthetic sweetener also being added.

These dihydrochalcones, their preparation and their use are further described in the following Examples. These are to illustrate the invention and are not to be construed as limitations on this invention, which is instead defined by the appended claims.

EXAMPLE I

This example describes the preparation of a derivatized dihydrochalcone in accordance with the present invention. In part A, an alkylating agent is prepared; in part B, alkylation is effected; and in part C, opening and reduction are set forth.

A. Into a 1,000 ml three-neck flask is charged 288.5 g of triphenylphosphine, and 96.0 g of 2-(2-methoxyethoxy) ethanol ($CH_3$—O—$C_2H_4$—O—$C_2H_4$—OH). The mixture is stirred and 178 g of N-bromosuccinimide is added over 1½ – 2 hours. The mixture warms and is stirred for ½ hour. It is then heated and a vacuum is pulled causing 138.5 g of an oil to distill overhead. This is collected and analyzed and found to be principally 2-(2-methoxyethoxy) ethyl bromide.. Redistillation yields this bromide in a pure form.

Next, 300 ml of methanol, 2.3 g of metallic sodium and 13.6 g of dimethyl malonate are combined; 18.3 g of the 2-(2-methoxyethoxy)ethyl bromide is added; and the mixture is refluxed overnight. Methanol is removed by vacuum evaporation, and a diester product, $CH_3$—O—$C_2H_4$—O—$C_2H_4$—$CH(CO_2CH_3)_3$, is recovered by vacuum distillation.

1.17 Grams of this ester is added to 1.12 g of potassium hydroxide in 12 ml of 1:1 methanol-water, and stirred for ½ hour. Methanol is removed and concentrated hydrochloric acid is added to pH 1. The mixture is extracted into ethyl acetate. The extract phase is dried and stripped of ethyl acetate to yield off-white crystals of the diacid $$CH_3-O-C_2H_4-O-C_2H_4-CH(CO_2H)_2.$$

0.94 Grams of this diacid is dissolved in diethyl ether. 0.732 Grams of bromine is added and the mixture is stirred and heated for about one hour. The mixture is washed with brine to remove HBr and dried over $MgSO_4$. Ether is removed, yielding crystals of the boromidiacid, $$CH_3-O-C_2H_4-O-C_2H_4-CBr(CO_2H)_2,$$

which heated at 130°–140° C for one hour to yield the bromomonoacid, $$CH_3-O-C_2H_4-O-C_2H_4-\underset{\underset{Br}{|}}{\overset{\overset{COOH}{|}}{CH}}\,,$$

which is isolated by vacuum distillation. This preparation is repeated on a larger scale to yield 3.3 g of the bromomonoacid, which is dissolved in 50 ml of dichloromethane. To this solution are added 5.6 ml of methanol and 94 mg of p-toluenesulfonic acid hydrate catalyst; and the mixture is refluxed overnight. The next day, the solvent is vacuum evaporated and the bromomonoester, $$CH_3-O-C_2H_4-CHBr-CO_2CH_3,$$

is recovered.

B. 28 Milligrams of anhydrous potassium carbonate, 60 mg of hesperetin, and 0.4 ml of dimethylformamide (DMF) are combined and stirred at room temperature. 102 Milligrams of the bromomonoester of part A are added along with 0.4 ml of DMF. The mixture is stirred for 23 hours and analyzed by thin layer chromatography and found to contain the flavanone alkylation product, which is recovered by extraction into ethyl acetate from water followed by drying and concentration and purification by preparative thin layer chromatography.

C. 58 Milligrams of the flavanone alkylation product of part B is dissolved in 5.0 ml of 5% potassium hydroxide. To this is added 25 mg of 5% Pd on charcoal, and the mixture is capped with an excess of hydrogen. The mixture stands at room temperature for 19 hours. It is filtered, acidified to pH 2 with 10% hydrochloric acid, and extracted with ethyl acetate. The extracts are dried and evaporated to yield a colorless oil, which is purified by preparatory scale thin layer chromatography to yield a product which is identified as the derivatized dihydrochalcone,

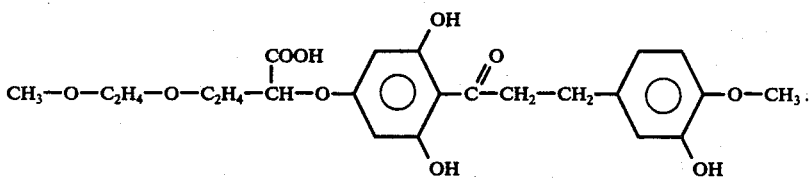

This material has a sweet taste. When prepared in larger amounts, it is added to soft drinks, coffee, cough syrups, gelatin desserts and other edible compositions in amounts of from about 0.0003% to 0.05% by weight to impart a sweet taste thereto.

EXAMPLE II

The experiment of parts B and C of Example I is repeated with one major change. As an alkylating agent is employed 2-bromoethylpropionate. The resulting final product is the dihydrochalcone

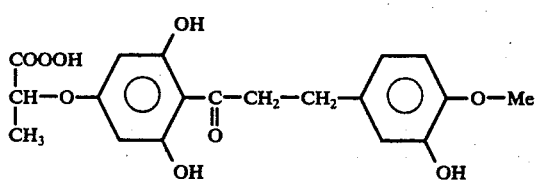

This product is sweet, and when added to edible compositions alone or in combination with saccharin or sugar, imparts a sweet taste to the edible compositions.

EXAMPLE III

Carbowax 350, $CH_3O(CH_2CH_2O)_n-CH_2CH_2OH$ (where $n \cong 7$), is converted in the same manner as described in Example I, Part A, to the corresponding bromo methyl ester derivative,

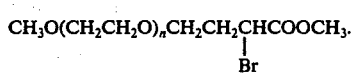

This material is used to alkylate hesperetin by the same procedure ($K_2CO_3$, DMF) as described in Example I, Part B, and the resulting ester hydrogenated in 5% aqueous KOH to the desired dihydrochalcone carboxylic acid,

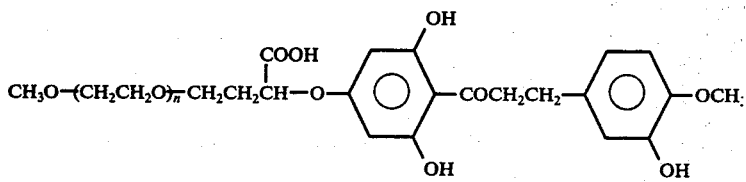

where $n \approx 7$, utilizing the procedure of Example I, Part C.

EXAMPLE IV

Hesperetin (125 mg) is dissolved in 5 ml of dry tetrahydrofuran, cooled to $\sim 0°$, and treated with one equivalent of sodium hydride (42.1 mg of 57% dispersion). After stirring at room temperature for 3 hours under an argon atomsphere, the reaction mixture is evaporated to dryness under reduced pressure.

The resulting sodium salt of hesperetin is added to 1 ml of freshly distilled glycidol and the mixture stirred at room temperature under an argon atmosphere for 30 hours. The unreacted monomer is removed by heating the reaction mixture at $\sim 0.5$ mm and 140° as described by S. Sandler and F. Berg in J. Polymer. Sci., I, pp. 1253-1259 (1966).

The resulting crude reaction mixture is purified by chromatography on Bio-Gel P-2 using 0.02 M phosphate buffer as the eluant.

After de-salting and freeze-drying of the desired fractions, the flavanone-polyether is converted to the desired dihydrochalcone

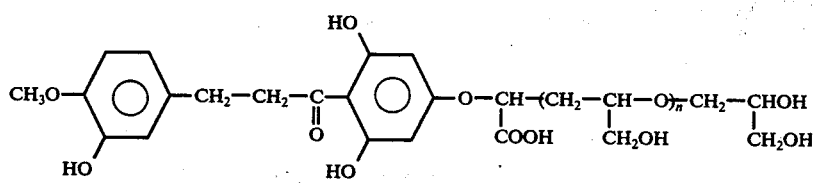

where $n \cong 5$ by hydrogenation in aqueous 5% KOH as described in the procedure of Example I, Part C.

We claim:

1. A compound of the formula

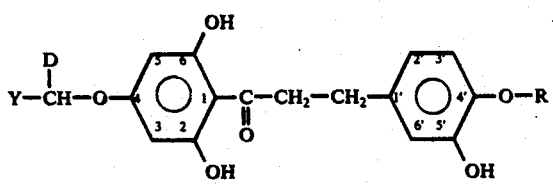

wherein Y is a sulfonic acid or a pharmacologically acceptable salt thereof, D is a linear polyether of the formula $CH_3-(O-CH_2-CH_2)_n-$ wherein $n$ has a value of from 1 to 30 inclusive, and R is a lower alkyl of from 1 to 4 carbon atoms inclusive.

2. The compound of claim 1 wherein R is methyl.

3. The compound of claim 2 wherein $n$ has a value of from 1 to about 7.

4. The compound of claim 3 wherein Y is sulfonic acid or a sodium or potassium salt thereof.

5. The compound of claim 4 wherein $n$ is 1.

6. A compound of the formula

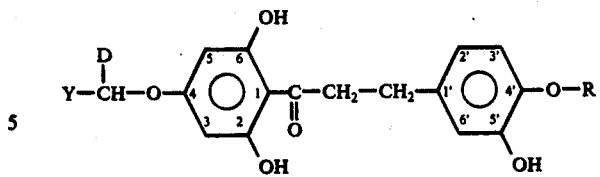

wherein Y is a sulfonic acid or a pharmacologically acceptable salt thereof, D is a polyglycidol ether of the formula

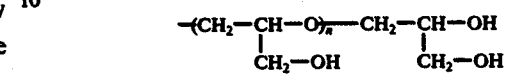

wherein $n$ equals about 5, and R is a lower alkyl of from 1 to 4 carbon atoms inclusive.

7. The compound of claim 6 wherein R is methyl and Y is a sulfonic acid or a sodium or potassium salt thereof.

8. A sweetened edible composition comprising an edible composition having in intimate admixture therewith from 0.0001% to about 0.05% by weight of a compound of claim 1.

9. The method of sweetening an edible composition comprising admixing with said edible composition from about 0.0001% to about 0.05% by weight of a compound of claim 1.

* * * * *